US008892384B2

United States Patent
Pado

(10) Patent No.: US 8,892,384 B2
(45) Date of Patent: Nov. 18, 2014

(54) SYSTEMS AND METHODS FOR PROVIDING TEMPERATURE COMPENSATION IN STRUCTURAL HEALTH MONITORING

(75) Inventor: Lawrence E. Pado, St. Charles, MO (US)

(73) Assignee: The Boeing Company, Chicago, IL (US)

( * ) Notice: Subject to any disclaimer, the term of this patent is extended or adjusted under 35 U.S.C. 154(b) by 365 days.

(21) Appl. No.: 13/163,116

(22) Filed: Jun. 17, 2011

(65) Prior Publication Data

US 2012/0323517 A1    Dec. 20, 2012

(51) Int. Cl.
| | |
|---|---|
| *G06F 19/00* | (2011.01) |
| *G06F 17/18* | (2006.01) |
| *G01N 29/32* | (2006.01) |
| *G01N 29/04* | (2006.01) |
| *G01N 29/38* | (2006.01) |
| *G01N 29/24* | (2006.01) |
| *G01M 7/00* | (2006.01) |
| *G01N 29/30* | (2006.01) |

(52) U.S. Cl.
CPC ............ *G01N 29/326* (2013.01); *G01N 29/043* (2013.01); *G01N 29/38* (2013.01); *G01N 2291/0258* (2013.01); *G01N 29/245* (2013.01); *G01M 7/00* (2013.01); *G01N 29/30* (2013.01)
USPC ............................................. 702/104; 73/1.82

(58) Field of Classification Search
CPC ........... G06F 19/00; G06F 17/18; G06F 3/16; G06F 11/3058; G01R 19/32; G01R 31/30; G01R 27/02; G01N 29/043; G01N 29/245; G01N 29/326; G01N 29/38; G01N 29/30
USPC ......................... 702/104, 56, 71, 159; 73/1.82
See application file for complete search history.

(56) References Cited

U.S. PATENT DOCUMENTS

| | | | |
|---|---|---|---|
| 5,965,817 | A | 10/1999 | Schwarz et al. |
| 7,930,128 | B2 | 4/2011 | Beard |

OTHER PUBLICATIONS

Y. Lu, "Analysis and modeling of diffuse ultrasonic signals for structural health monitoring", Ph.D. thesis, Georgia Institute of Technology, Aug. 2007.*
W. Adams, et al., "Correlator compensation requirements for passive time-delay estimation with moving source or receivers", IEEE 1980.*
Lu, Y. et al.; A Methodology for Structural Health Monitoring with Diffuse Ultrasonic Waves in the Presence of Temperature Variations; Ultrasonics; vol. 43; 2005; pp. 717-731.
Search Report for Application No. GB1210820.5; Oct. 1, 2012; 4 pages.

* cited by examiner

*Primary Examiner* — Eliseo Ramos Feliciano
*Assistant Examiner* — Ruihua Zhang
(74) *Attorney, Agent, or Firm* — Armstrong Teasdale LLP

(57) ABSTRACT

A method for compensating for environment induced variations in structural health monitoring data is described. The method includes imparting a vibration onto a structure first location, the structure at a first temperature, receiving a comparison signal resulting from the vibration at a second location, accessing data representing a reference signal previously received at the second location, based on vibration at the first location, the reference signal received when the structure was at a second temperature, dividing the signals across multiple time windows, performing a cross correlation between the signals in each window to maximally correlate the signals within each window, performing a weighted regression on time to estimate time shift, the weights based on reference signal energy in each window, to determine a relationship between time and time shift, and using the relationship between time and time shift of the comparison signal to reduce the effects of environment on the comparison signal.

12 Claims, 15 Drawing Sheets

SYSTEMS AND METHODS FOR PROVIDING TEMPERATURE COMPENSATION IN STRUCTURAL HEALTH MONITORING

BACKGROUND

The field of the disclosure relates generally to structural health monitoring, and more specifically, to systems and methods for providing temperature compensation in structural health monitoring.

Many structural health monitoring (SHM) systems operate by producing a vibration signal, for example by exciting a piezo-electric (PZT) actuator bonded to a structure, and then reading that signal with a PZT sensor bonded at a separate location. Any damage that has occurred between the two PZT transducers will change the characteristics of the transmitted signal, as compared to the characteristics of a transmitted signal where no damage has occurred between the two transducers.

Many SHM algorithms work in the time domain by comparing a reference, or baseline, signal with a comparison signal that may be indicative of damage. In a properly operating SHM system, the degree of difference between the two signals is proportional to the size of damage in the structure. Examples of damage in such structures include a crack having a length or a delamination area within the structure.

Although there are many ways to measure the difference between two signals, normalized RMS error is one very common measure. The RMS error is calculated by subtracting the comparison signal from the reference signal forming an error signal. Each sample of this error signal is squared and summed. The result is divided by the number of samples to get the mean square value and the square root of this value is taken. This is the Root Mean Square or RMS of the error signal. This number is then normalized by the RMS value of the reference wave.

Unfortunately damage is not the only variable that can change a signal. A real world effect that strongly affects a signal is the temperature of the structure when the PZT actuator produces the signal and the PZT sensor measures the signal. One effect of temperature change is to stretch (heating) or compress (cooling) the signal with a secondary effect of distorting the shape of the signal. Due to this effect, the mean squared error between two waveforms recorded at temperatures only a few degrees apart is of the same order of magnitude as the mean squared error between waveforms recorded from a structure before and after damage.

BRIEF DESCRIPTION

In one aspect, a method for compensating for environment induced variations in structural health monitoring application data is provided. The method includes imparting a vibration signal onto a structure at a first location, the structure at a first temperature, receiving a comparison signal at a second location of the structure, the comparison signal resulting from the vibration signal, accessing data representing a reference signal, the reference signal previously received at the second location, based on an imparted vibration at the first location, the reference signal received when the structure was at a second temperature, dividing the comparison signal and the reference signal across a plurality of time windows, performing a cross correlation between the comparison signal and the reference signal in each time window by recording an amount of time shift required to maximally correlate the comparison signal and the reference signal within each time window, performing a weighted regression on time to estimate time delay, the weights based on a relative amount of signal energy from the reference signal in each time window, to determine a relationship between time and time shift as a quadratic or higher order equation, and using the determined relationship between time and time shift of the comparison signal to reduce the effects of environment on the comparison signal.

In another aspect, one or more computer-readable storage media having computer-executable instructions embodied thereon are provided, wherein when executed by at least one processor, the computer-executable instructions cause the at least one processor to receive comparison signal data relating to a vibration experienced at a location of a structure, the comparison signal data resulting from a vibration signal imparted onto the structure at a different location, the comparison signal data generated when the structure is at a first temperature, access data representing a reference signal, the reference signal previously received at the structure location, and also based on an imparted vibration at the different location, the reference signal received when the structure was at a second temperature, divide the comparison signal and the reference signal across a plurality of time windows, perform a cross correlation between the comparison and reference signals in each of the time windows by recording an amount of time shift required to maximally correlate the two signals within each time window, perform a weighted regression, the weights based on the relative amount of signal energy from the reference signal in each time window, to determine a relationship between time and time delay as a quadratic or higher order equation, and use the relationship between time and time delay to reduce the effects of environment on the comparison signal.

In still another aspect, a method of compensating for temperature effects in a structural health monitoring system is provided. The method includes compensating for nonlinear phase changes in a comparison signal, as compared to a reference signal, wherein a phase shift factor is replaced with a general function, implementing a weighted regression of time shifts associated with the comparison signal across each of a plurality of time windows to determine parameters of the general function, implementing a time-shift outlier correction process onto the weighted regression, and processing the comparison signal using the general function and the parameters determined for the general function to provide output corresponding to a reduction in a stretch or a compression of the reference signal and the comparison signal.

The features, functions, and advantages that have been discussed can be achieved independently in various embodiments or may be combined in yet other embodiments further details of which can be seen with reference to the following description and drawings.

DETAILED DESCRIPTION

As stated above, the temperature of the structure when the PZT actuator produces the signal and the PZT sensor measures the signal can affect test measurements and results in a phase change of the signal with respect to the original temperature. For a given temperature change, this can be modeled as $y(t)=x(t-\zeta t)$ (Equation 1), where $\zeta$ is the phase shift factor.

Figure 1:
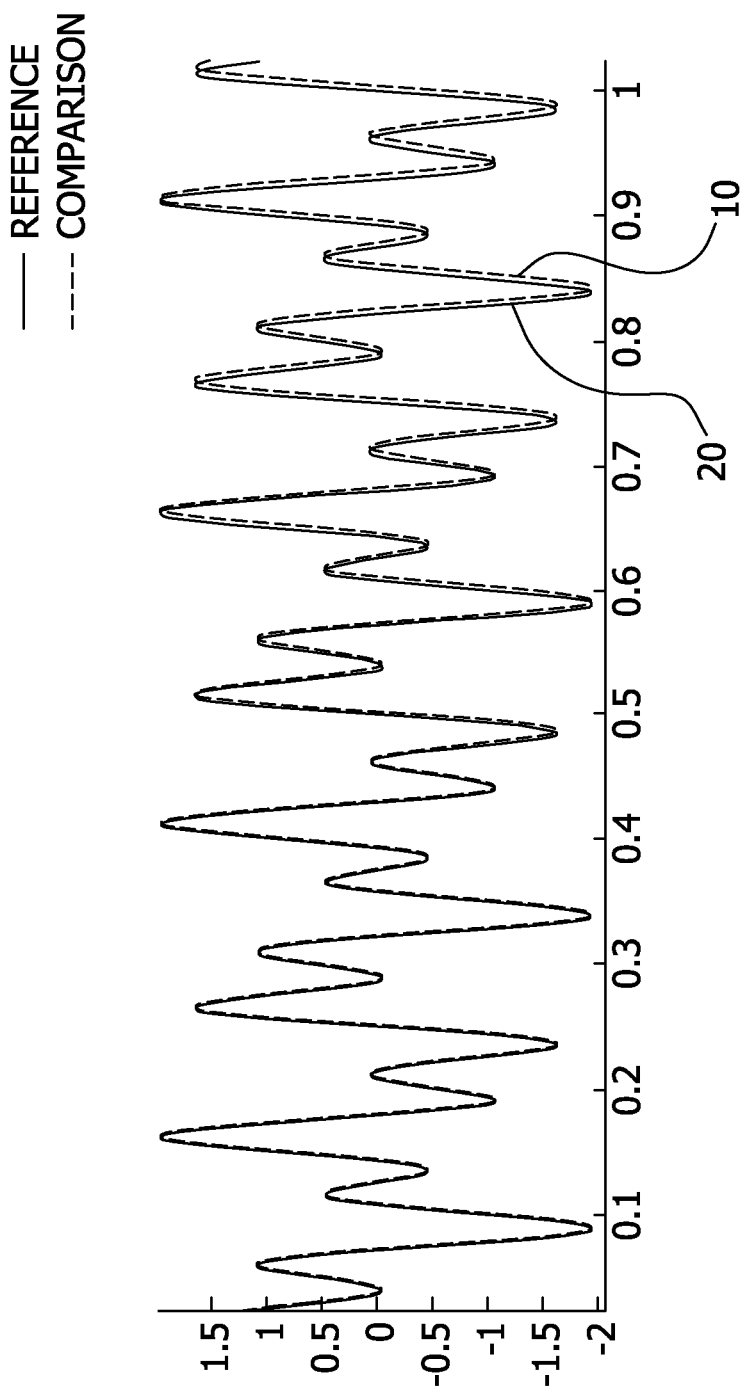
FIG. 1 is a graph illustrating simulated PZT sensor data, a reference signal received from the sensor at one temperature, and a comparison signal received from the sensor at a different temperature.

Equation 1 can be understood better by examining FIG. 1, which illustrates two sets of simulated PZT sensor data taken at different temperatures. The comparison signal 10 appears to be a stretched version of the reference signal 20. In FIG. 1 it is clear that at the beginning, the comparison signal 10 and the reference signal 20 are nearly identical and lie directly on one another. As time passes, however, the comparison signal 10 appears to be stretching away from the reference signal 20, with more stretching occurring as additional time passes. This stretching is commonly referred to as phase shift as measured by time delay.

Figure 2:
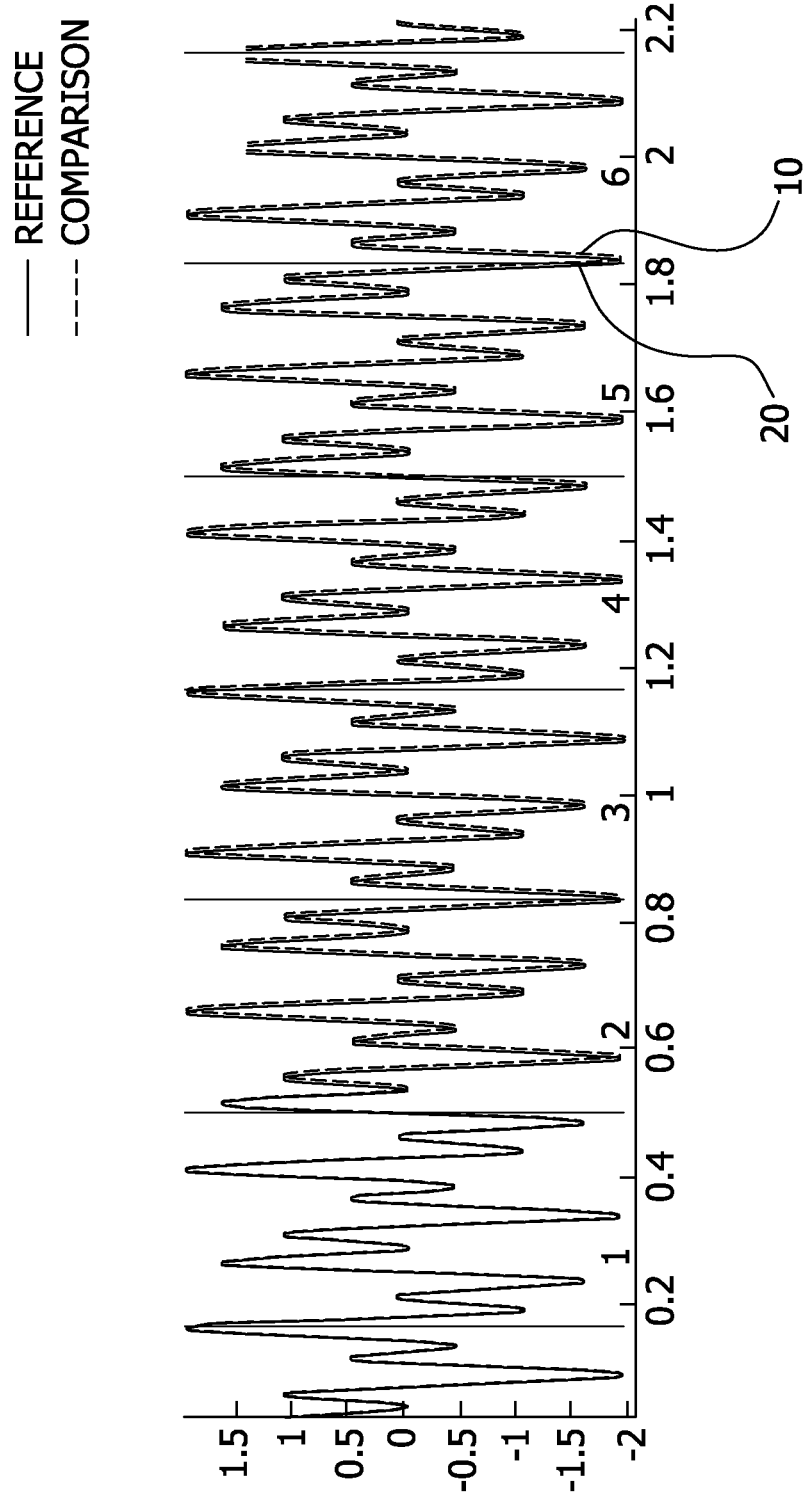
FIG. 2 is an illustration of the waveforms of FIG. 1 divided into multiple time windows.

FIG. 2 is an illustration of the waveforms (comparison signal 10 and reference signal 20) of FIG. 1 divided into multiple time windows. The amount of time delay associated with each window can be calculated. As shown in FIG. 2, the amount of time delay is greater in each succeeding window.

Figure 3:
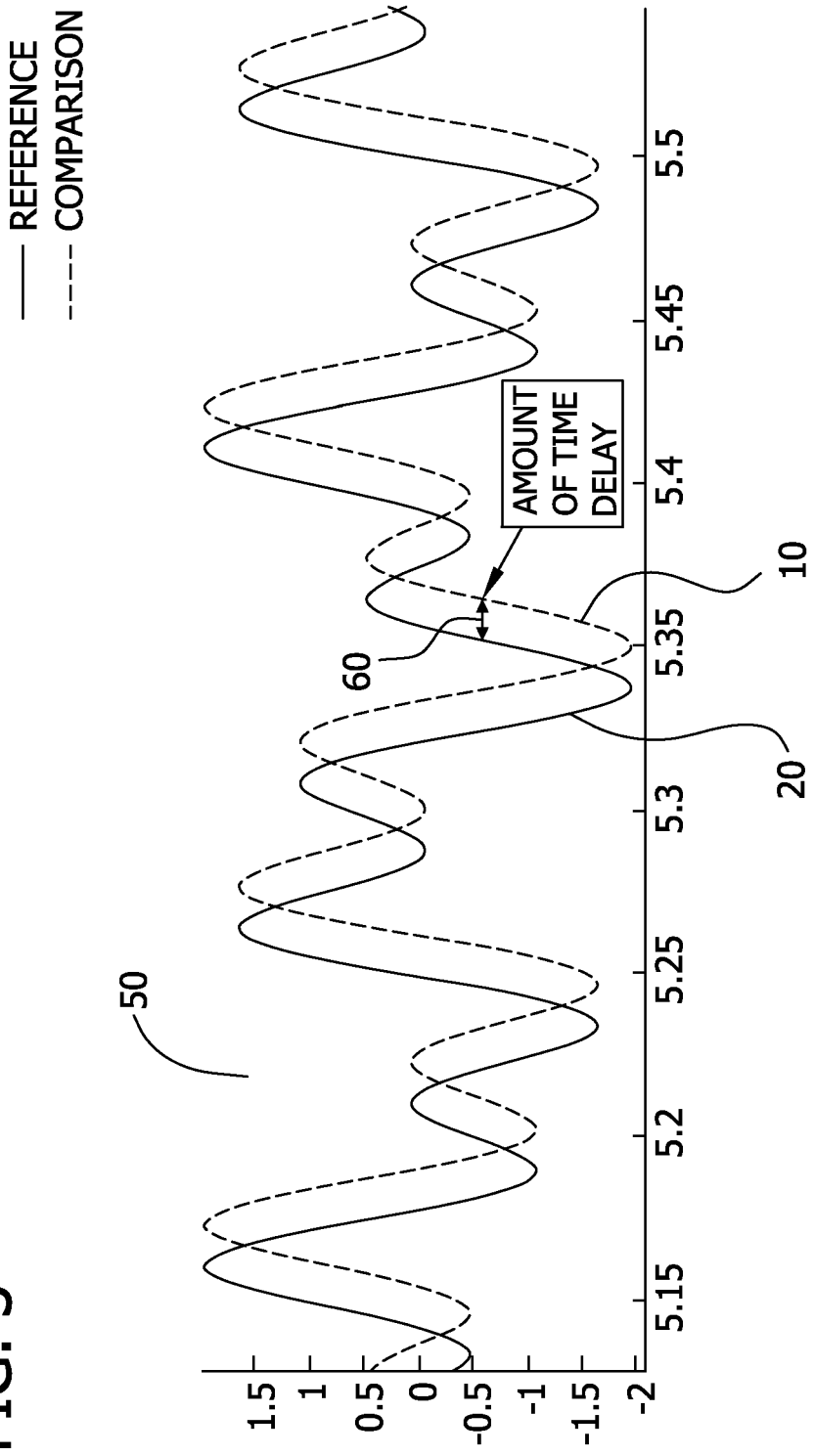
FIG. 3 is a magnified illustration of a single time window from FIG. 2.

FIG. 3 is a magnified illustration of a single time window 50 from FIG. 2. The reference signal 20 and the comparison signal 10 are magnified. The double headed arrow 60 denotes the amount of time delay in time window 50. The amount of time it would take to shift the comparison signal 10 to make it coincident with the reference signal 20 is the measure of time delay. This calculation is done using a short time cross correlation.

Figure 4:
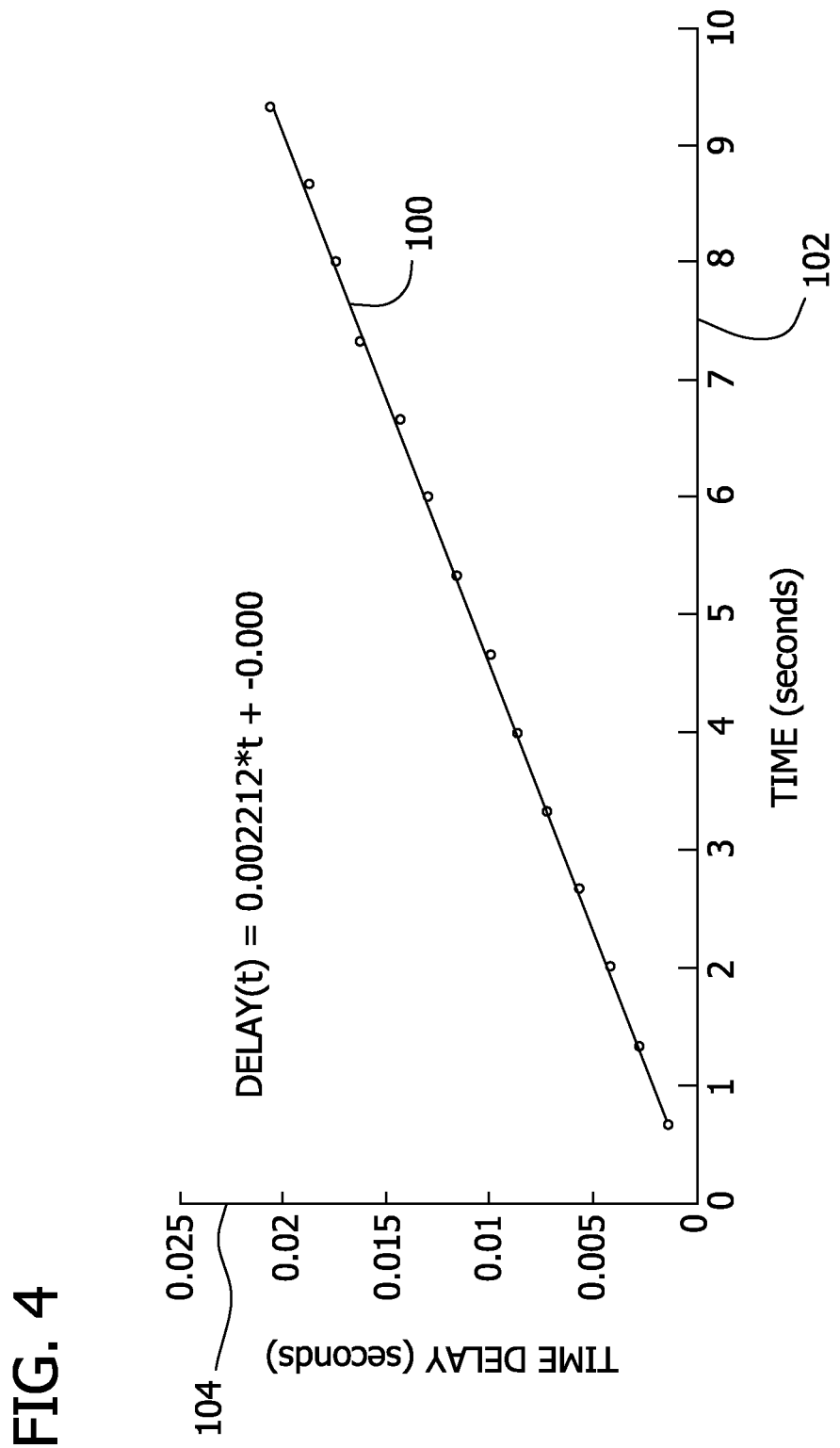
FIG. 4 illustrates a plot of time against time-shift for a fourteen window sample of a comparison signal and a reference signal.

FIG. 4 illustrates a plot 100 of time 102 against time shift 104 for a fourteen window sample of comparison signal 10 and reference signal 20. By performing a linear regression, time shift as a function of time can be calculated. Note that the phase shift factor $\zeta$ (per Eq. 2) has been calculated as the coefficient of t in FIG. 4 and has the value of 0.002212.

Issues in calculating the phase shift factor can occur under various adverse conditions. For example, large defects in a structure have been shown to produce erroneous estimates (e.g., outliers) of time shift in various time windows. These outliers, if left in the data set skew the estimate of the phase shift factor and therefore result in poor temperature compensation. One method to remove such outliers is to use only the first half of the waveform. A second method is to set an upper limit on the maximum values of the calculated time delay based on cross correlating adjacent (temperature-wise) baseline waveforms which are presumed to provide a basis for a clean calculation.

Robust Temperature Compensation for Non-Homogenous Structures and Noisy Environments The process set forth above, as well as the described methods to remove outliers, are insufficient for providing temperature compensation in composite structures, especially when there is more than a 10 degree C. temperature change between each baseline waveform. A number of improvements have been made to in order to provide temperature compensation under more difficult conditions. These difficult conditions include large defects, large temperature differences between the two waveforms, and non-homogenous structure such as those made from composite materials.

Figure 5:
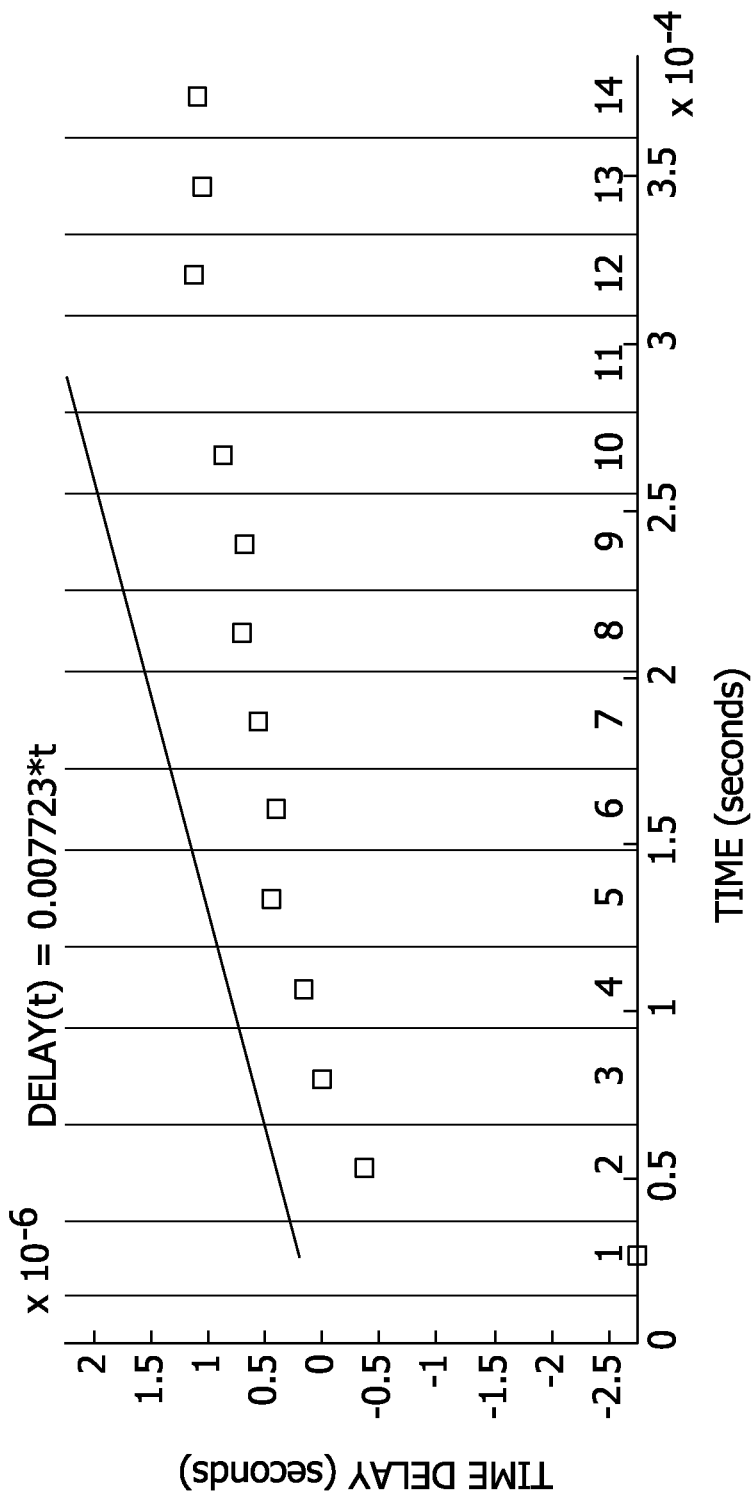
FIG. 5 illustrates a plot of time against time-shift for the fourteen window sample of a comparison signal and a reference signal of FIG. 4, and further illustrates a bias in calculated phase shift when it is assumed that time delay at time zero is zero.

$y(t)=x(t-\zeta t)$ makes the implicit assumption that the time shift at time-zero is 0.0. As shown in FIG. 5, making this assumption in all cases will cause a bias in the calculated phase shift and will result in inaccurate temperature compensation. One known cause of this bias is caused by hardware time delays in reporting true excitation start times. In other cases it may simply be convenient to truncate a small portion of the start of the waveform to remove corrupted signal.

Figure 6:
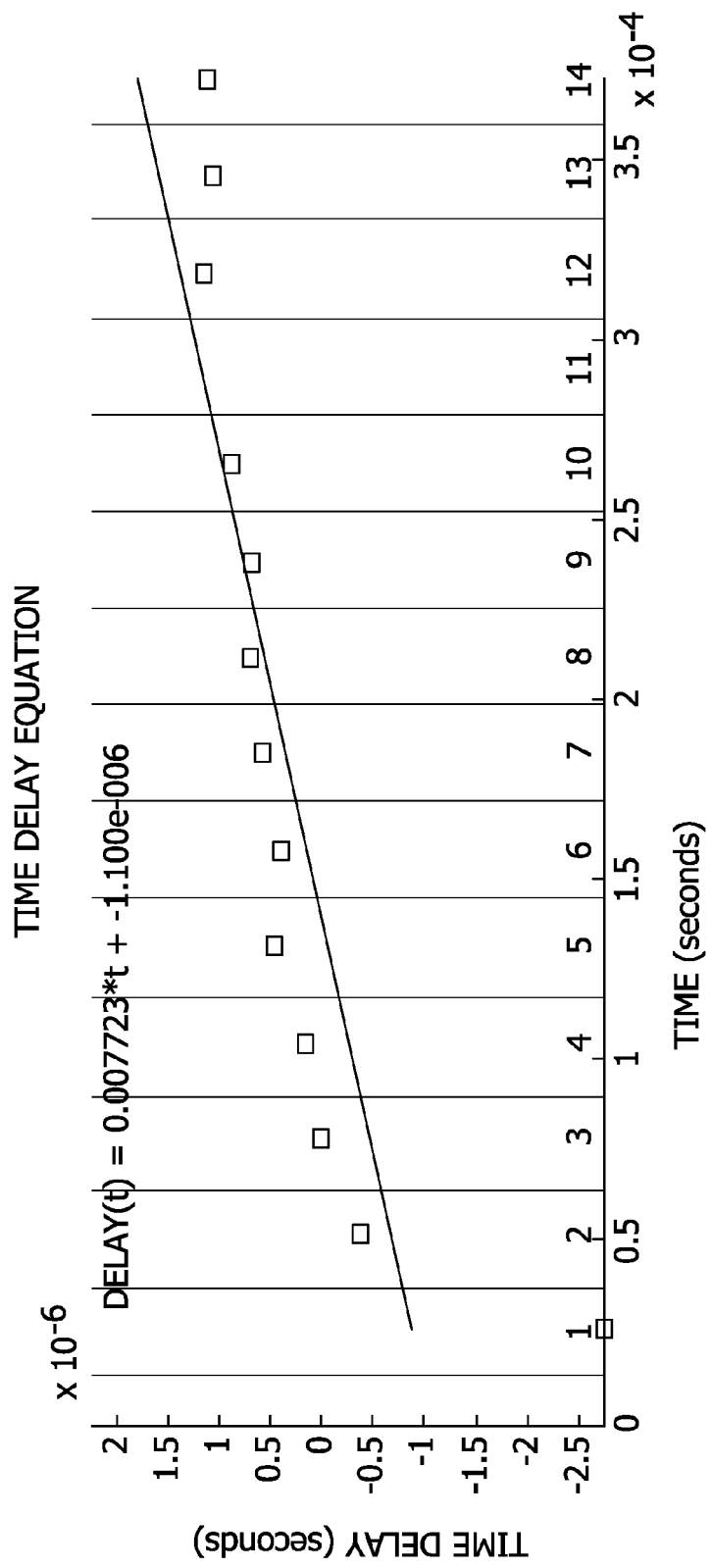
FIG. 6 is illustrates incorporation of the intercept which leads to a removal of the bias in phase shift that is illustrated in FIG. 5.

In any case the phase shift factor is replaced with a more general function of time, 't', as follows: $y(t)=x(t-f(t))$, with $f(t)$ being $\zeta t+\phi$, where $\zeta$ represents the slope of the time delay curve and $\phi$ is the curve intercept accounting for any system biases. FIG. 6 illustrates incorporation of the intercept which leads to a removal of the bias in phase shift. It is noted that the time against time shift line now passes through the data points.

Figure 7:
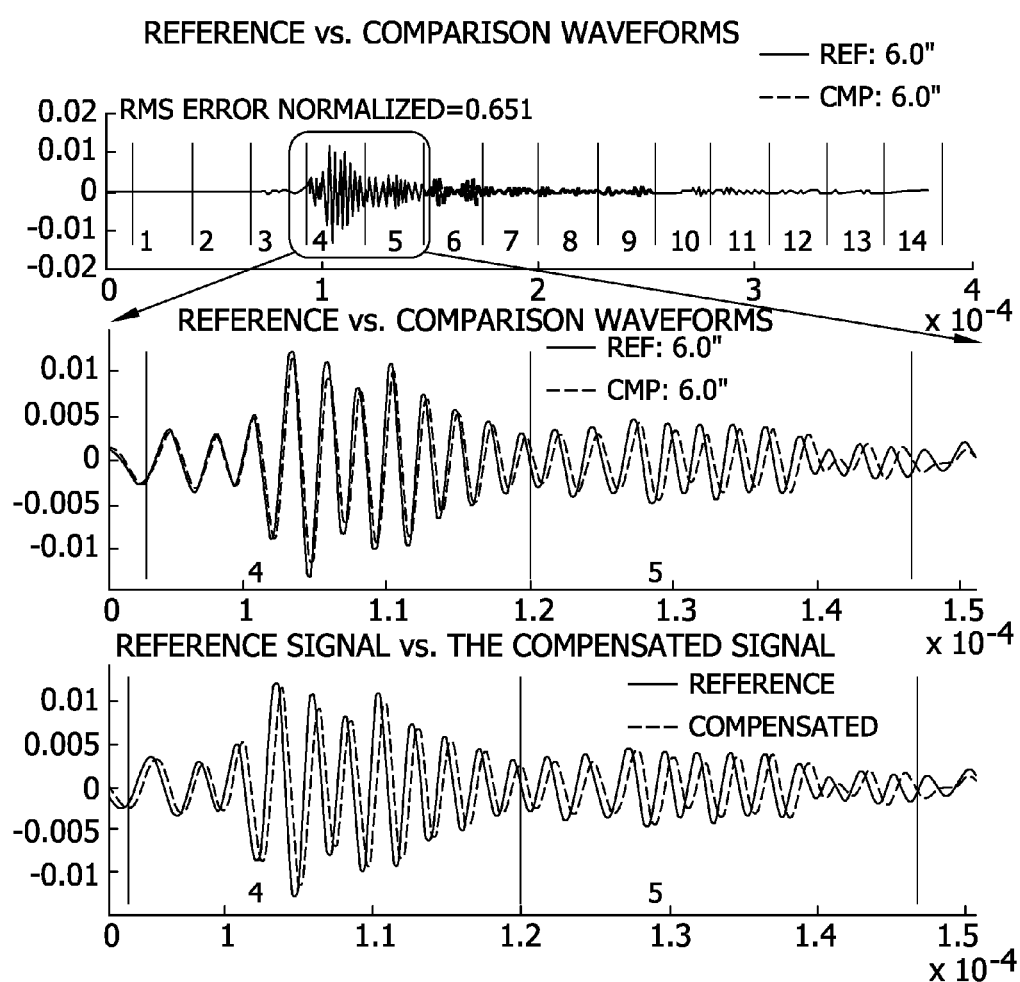
FIG. 7 illustrates that removal of the bias in the phase shift estimation is not enough, alone, to provide good compensation.
Figure 8:
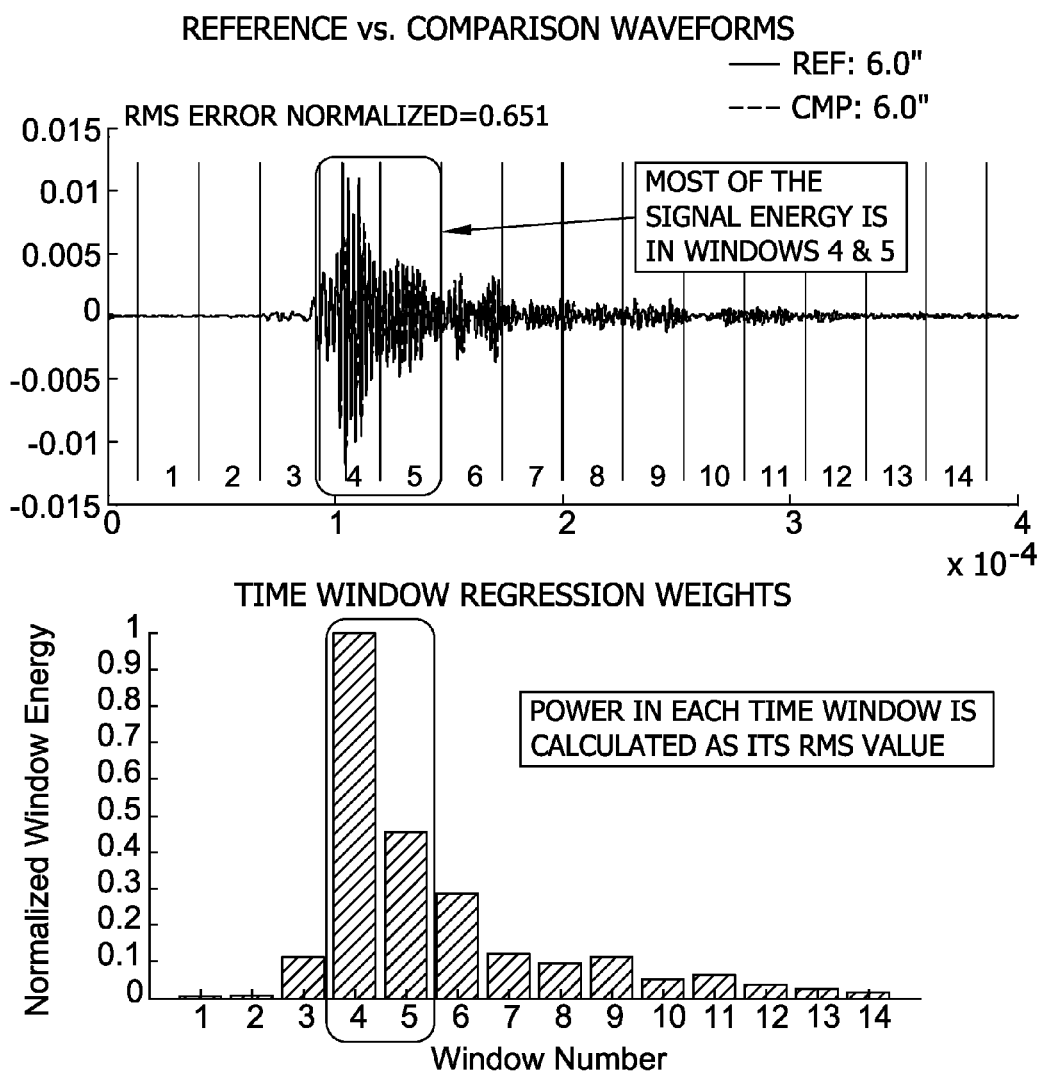
FIG. 8 illustrates that the majority of the signal energy is contained within the fourth and fifth time windows of the fourteen widow sample.

Although this method removes the bias in the phase shift estimation, it alone is not enough to provide good compensation as shown in FIG. 7. The reason this compensation worked so poorly is due to the important fact that each time delay data point is treated as equally important despite the fact that a minority of the points represent most of the energy in the signal. Examining FIG. 8, it is clear that most of the signal energy is contained within the fourth and fifth time windows. If the compensation is off in those windows, there will be a large difference in the normalized RMS error, whereas if the compensation were off in windows 1, 13, and 14, it would hardly register in the error.

What is needed then is a way to emphasize data points in high energy time windows and place less emphasis on time delay data points in low energy time windows. This emphasis and reduction in emphasis is accomplished using a technique called weighted regression. Weighted regression is a technique that emphasizes some data points over others by weighting each data point with a weight 'W' according to some criterion. Weighted regression has the effect of replicating each data point 'W' times. Determining what the weights should be has a large impact on the effectiveness of this approach.

In regard to the SHM application described herein, the normalized RMS values of the reference signal contained in each window are used as the weights although the comparison signal could be used instead. Using these values as weights properly rewards and penalizes each time delay data point according to its energy (importance).

Figure 9:
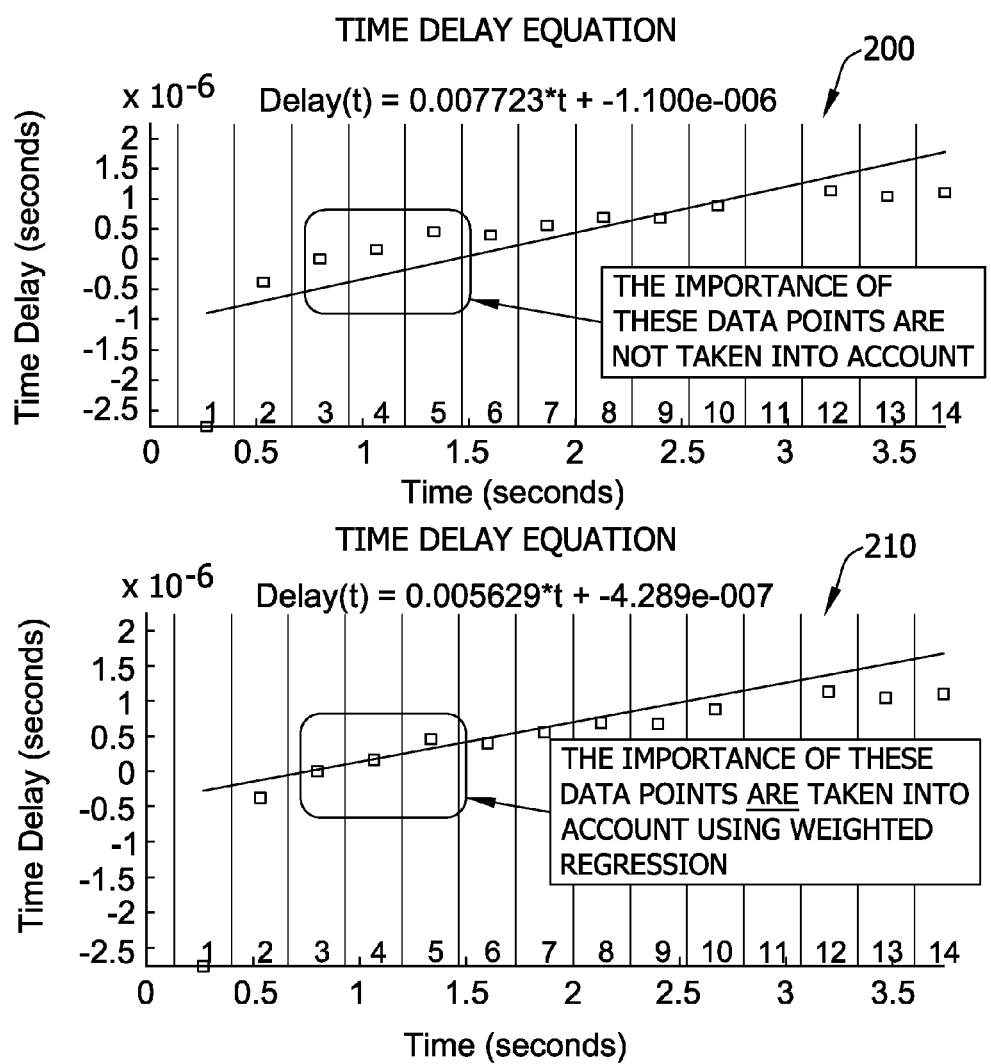
FIG. 9 illustrates the use of weighted regression for placement of the phase shift line.

Using weighted regression on time to estimate time delay, with the weights based on a relative amount of signal energy from the reference signal in each time window, the new placement of the phase shift line is shown in FIG. 9. Note that the three most important points in terms of energy are all well above the line in the top graph 200 of FIG. 9. Graph 200 is compared to the bottom graph 210 of FIG. 9 where the energy of the time windows is taken into account. It is noted how the line in graph 210 now passes through or very near each point.

Figure 10:
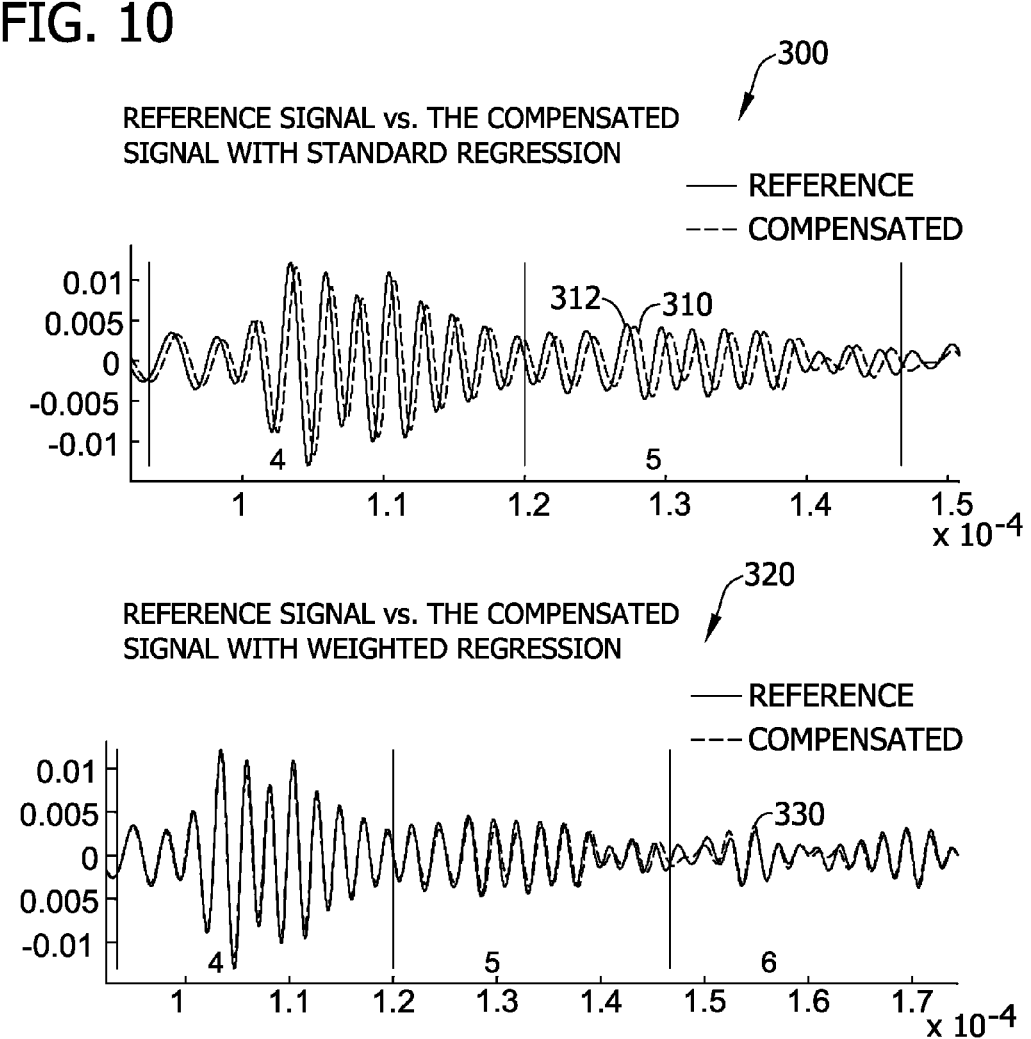
FIG. 10 shows, in a top graph, a wave against a reference wave with the time delay curve calculated with standard regression, and in a bottom graph, a properly compensated wave against the reference wave, the properly compensated wave generated using weighted regression.

Performing the temperature compensation process with this newly generated time delay line produces a very good compensated signal as is shown in FIG. 10. Specifically, the top graph 300 shows the poorly compensated wave 310 against a reference wave 312 with the time delay curve calculated with standard regression. The bottom graph 320 shows a properly compensated wave 330 that was generated using the regressing line generated using weighted regression.

Under various adverse conditions such as non-homogenous structures such as composites, large damage sites, or large temperatures differentials, time delay data points can be calculated that don't follow the trend of other data points. These outliers can skew the regression line and lead to poor temperature compensation. For example, FIG. 11 illustrates an outlier 350 produced in time window number 10 and how it skews the resultant regression line 352 down, away from the rest of the data points.

Noting that a temperature change produces changes that are either all stretching or all compressing suggests a way to correct for these outliers. First, the time delay data point associated with highest window energy is most likely to be calculated correctly due to its very high signal to noise ratio. Deformations caused by defects or material characteristics will have the smallest overall affect on these high energy waveforms. Thus it can be established if the waveform is stretching at all points or contracting at all points. Once any stretching or contracting has been established, a short time cross correlation algorithm can be run, and run only on those signal points consistent with the observation. In other words, the comparison waveform either slides to the left to become coincident or it slides to the right. The high energy portion of the waveform determines in which direction the waveform should slide.

Figure 11:
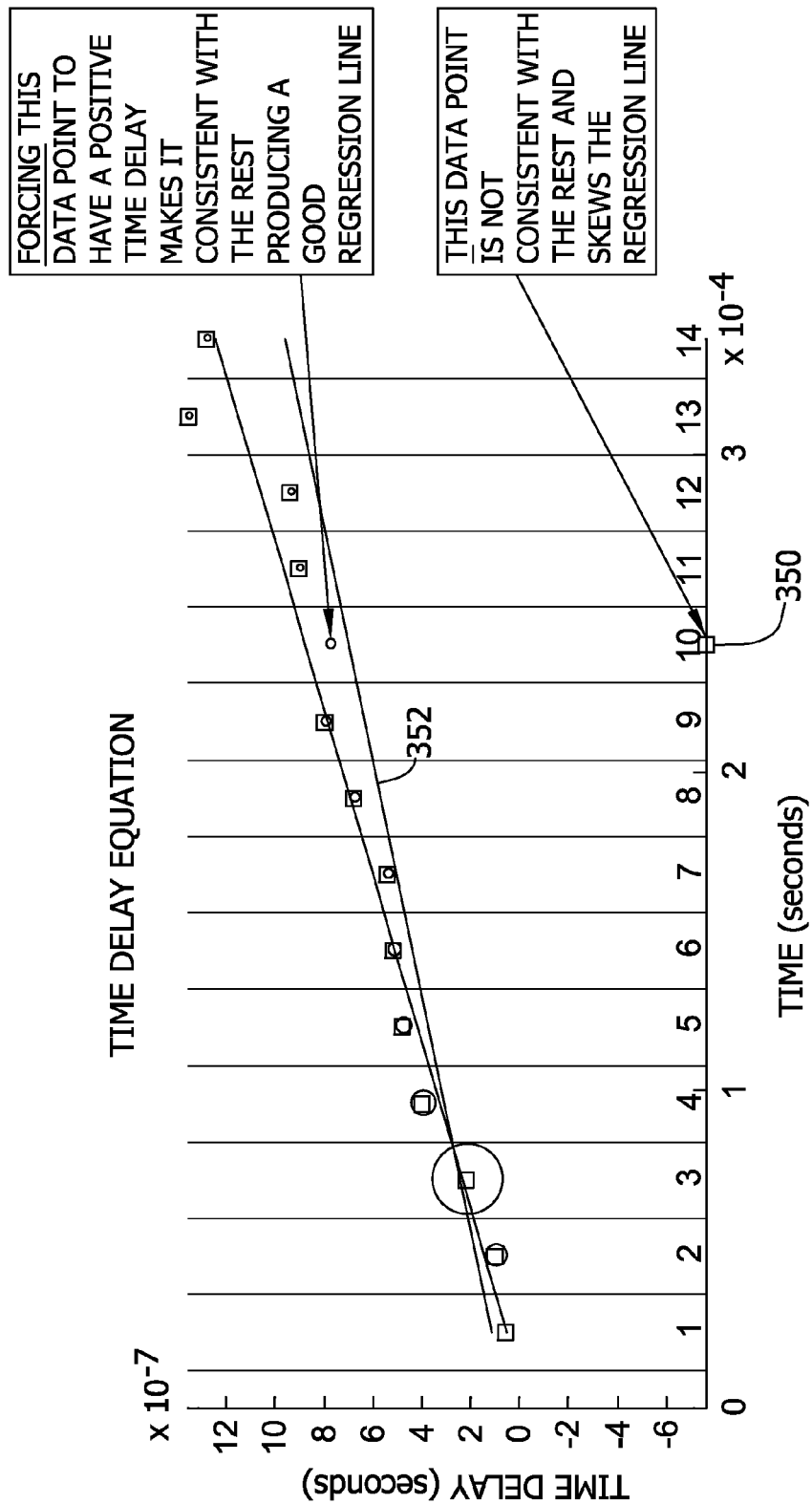
FIG. 11 illustrates a outlier produced in the tenth time window number of the fourteen window sample and how the outlier skews the resultant regression line down, away from the rest of the data points.

FIG. 11 shows the point of highest correlation for a positive time delay lies close to the trend of the other points. The regression lines calculated from these corrected points provides for good temperature compensation.

Non-Linear Functional Representation of Time Delay

Figure 12:
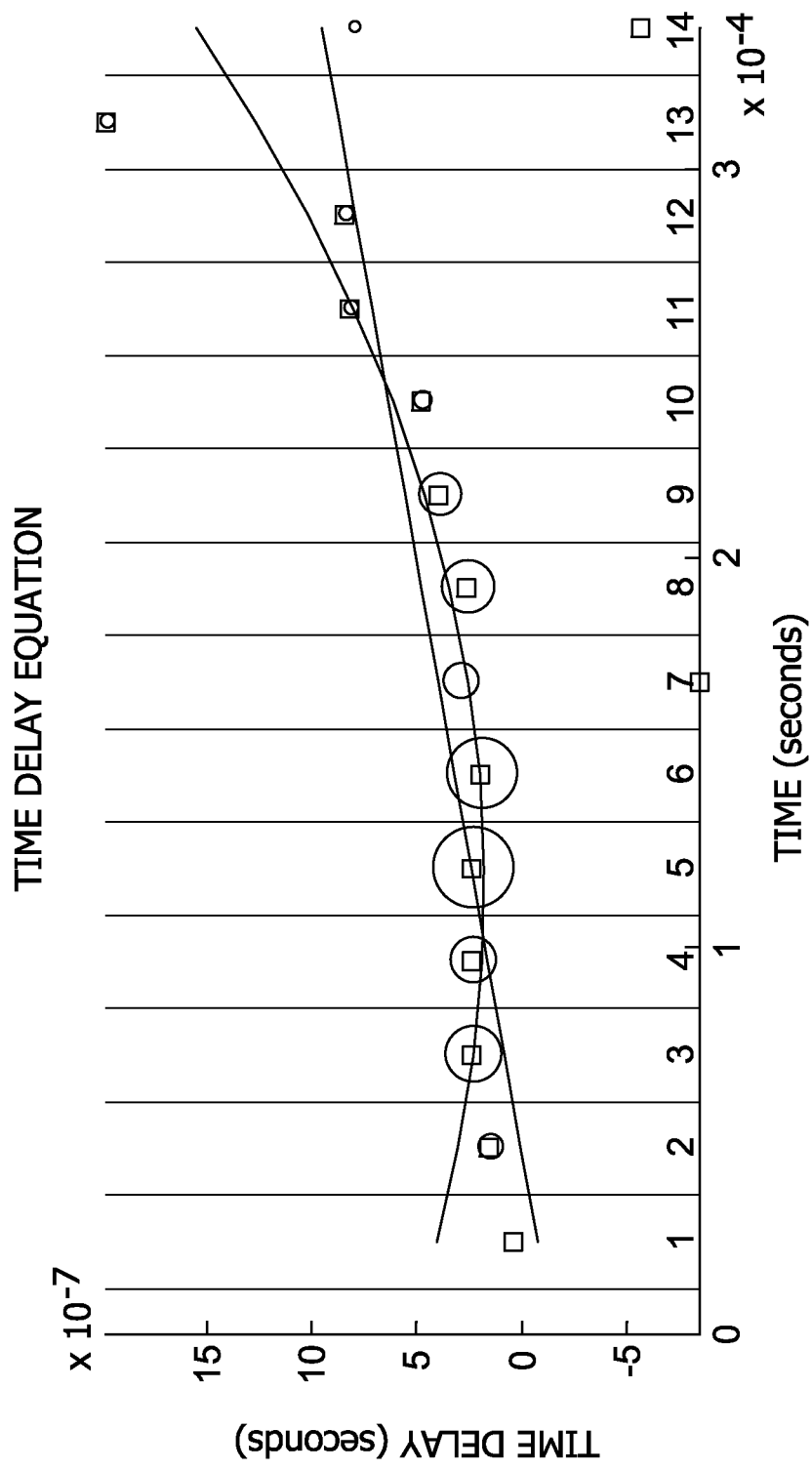
FIG. 12 illustrates that the pattern of time delay with respect to time is strongly curved for non-homogenous structure such as composites.

Although in homogenous structures such as aluminum the time delay is linear with respect to time, this is not always the case for non-homogenous structure such as composites. As shown in FIG. 12, the pattern of time delay with respect to time is strongly curved. While a linear fit using weighted regression will correctly compensate the fifth time window of FIG. 12, most of the rest of the waveform will be poorly compensated. One solution is to replace the $f(t)$ in $y(t)=x(t-f(t))$ with a $f(t)$ capable of modeling nonlinear behavior. Once such formula is $f(t)=\alpha t^2+\zeta t+\phi$, which leads to $y(t)=x(t-(\alpha t^2+\zeta t+\phi))$ which models time delay as a quadratic function of time. In one alternative of this embodiment, the formula may model as a higher order equation.

Using $f(t)=\alpha t^2+\zeta t+\phi$ to generate the regression curve leads to an accurate representation of the time delay data and thus a good temperature compensation obtained using $y(t)=x(t-(\alpha t^2+\zeta t+\phi))$.

The described embodiments provide temperature compensation improvements when interpreting SHM data by reducing the effects of environment on the comparison signal. For example, one improvement relates to replacing the phase shift factor $\xi$ with a general function $f(t)$, specifically $y(t)=x(t-(\alpha t^2+\zeta t+\phi))$. This configuration change compensates for non-linear phase changes in nonhomogenous structures and removes time delay biases.

Implementation of weighted regression using time window energy as the relative weighting function maximizes the effectiveness of the compensation by focusing on the most important sections of the signal and by eliminating a need to use the 'first half of signal' as described above. In addition, an implementation related to forced time delay consistency provides a robust outlier elimination process independent of the need for additional baselines.

Figure 13:
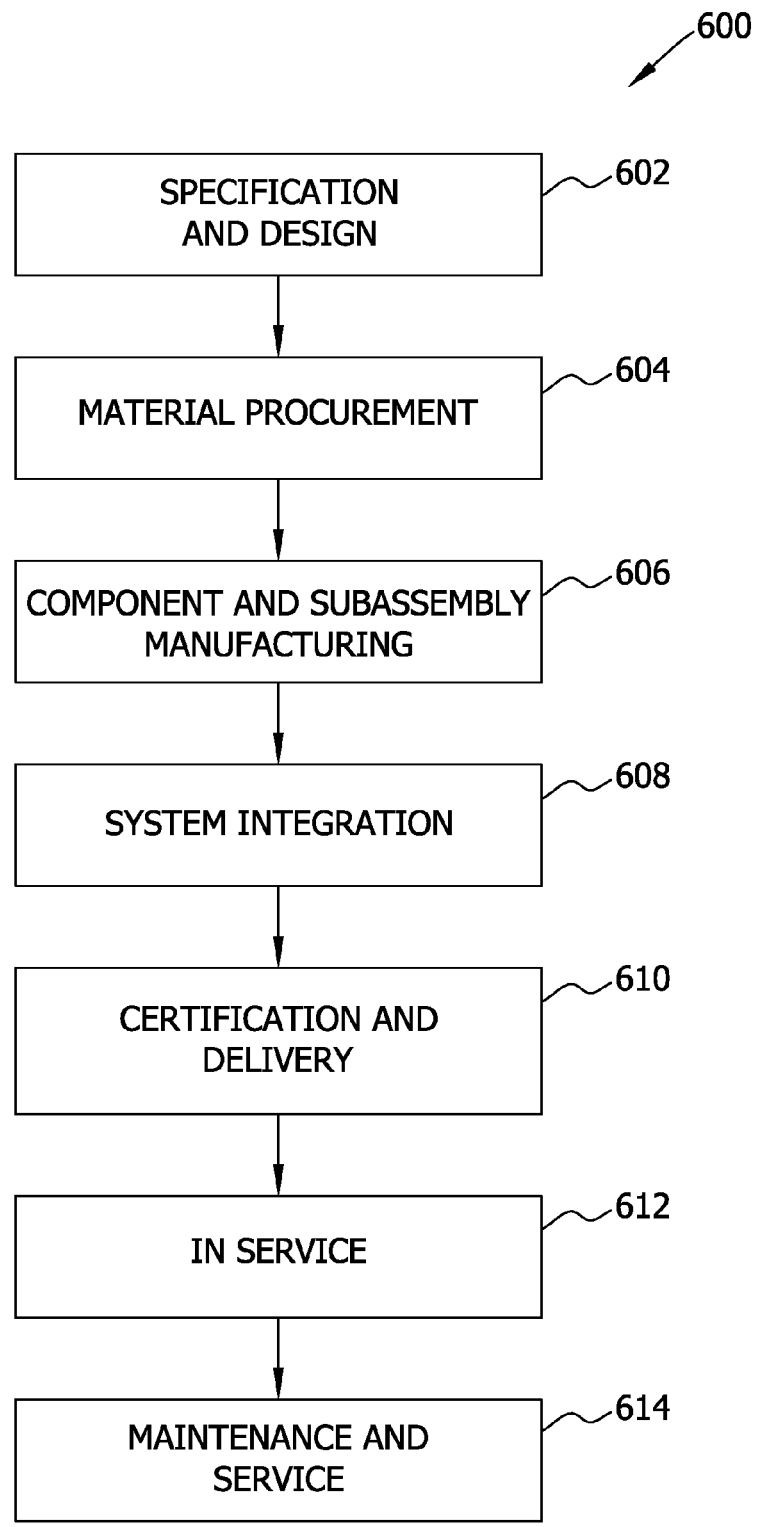
FIG. 13 is a flow diagram of an aircraft production and service methodology.
Figure 14:
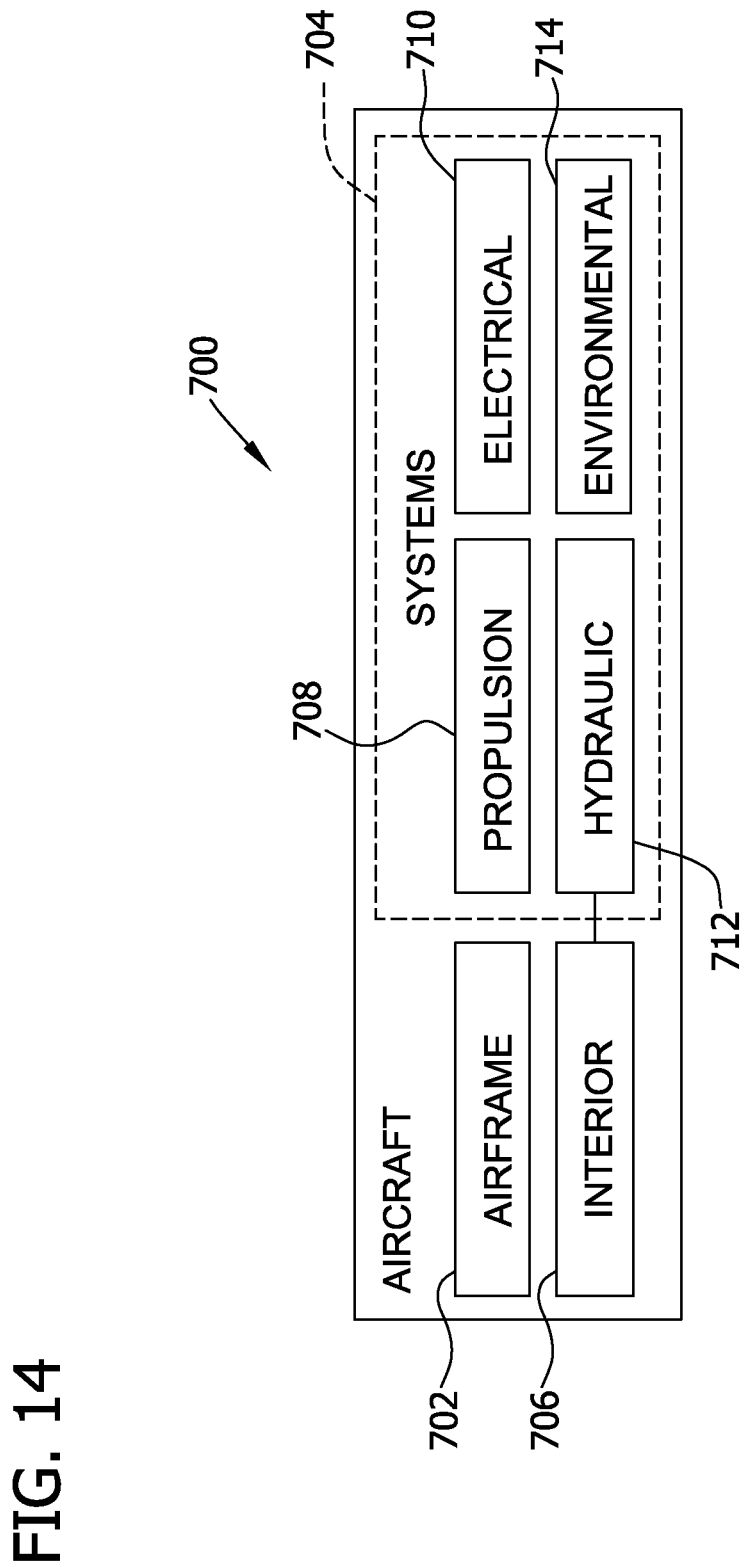
FIG. 14 is a block diagram of an aircraft.

Embodiments of the disclosure may be described in the context of aircraft manufacturing and service method 600 as shown in FIG. 13 and an aircraft 700 as shown in FIG. 14. During pre-production, aircraft manufacturing and service method 600 may include specification and design 602 of aircraft 700 and material procurement 604.

During production, component and subassembly manufacturing 606 and system integration 608 of aircraft 700 takes place. Thereafter, aircraft 700 may go through certification and delivery 610 in order to be placed in service 612. While in service by a customer, aircraft 700 is scheduled for routine maintenance and service 614 (which may also include structural health monitoring (SHM), modification, reconfiguration, refurbishment, and so on).

Each of the processes of aircraft manufacturing and service method 600 may be performed or carried out by a system integrator, a third party, and/or an operator (e.g., a customer). For the purposes of this description, a system integrator may include, without limitation, any number of aircraft manufacturers and major-system subcontractors; a third party may include, for example, without limitation, any number of venders, subcontractors, and suppliers; and an operator may be an airline, leasing company, military entity, service organization, and so on.

As shown in FIG. 14, aircraft 700 produced by aircraft manufacturing and service method 600 may include airframe 702 with a plurality of systems 704 and interior 706. Examples of systems 704 include one or more of propulsion system 708, electrical system 710, hydraulic system 712, and environmental system 714. Any number of other systems may be included in this example. Although an aerospace example is shown, the principles of the disclosure may be applied to other industries, such as the automotive industry.

Apparatus and methods embodied herein may be employed during any one or more of the stages of aircraft manufacturing and service method 600. For example, without limitation, components or subassemblies corresponding to component and subassembly manufacturing 606 may be fabricated or manufactured in a manner similar to components or subassemblies produced while aircraft 200 is in service.

Also, one or more apparatus embodiments, method embodiments, or a combination thereof may be utilized during component and subassembly manufacturing 606 and system integration 608, for example, without limitation, by substantially expediting assembly of or reducing the cost of aircraft 700. Similarly, one or more of apparatus embodiments, method embodiments, or a combination thereof may be utilized while aircraft 700 is in service, for example, without limitation, to maintenance and service 614 may be used during system integration 608 and/or maintenance and service 614 to determine whether parts may be connected and/or mated to each other.

The description of the different advantageous embodiments has been presented for purposes of illustration and description, and is not intended to be exhaustive or limited to the embodiments in the form disclosed. Many modifications and variations will be apparent to those of ordinary skill in the art. Further, different advantageous embodiments may provide different advantages as compared to other advantageous embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

Figure 15:
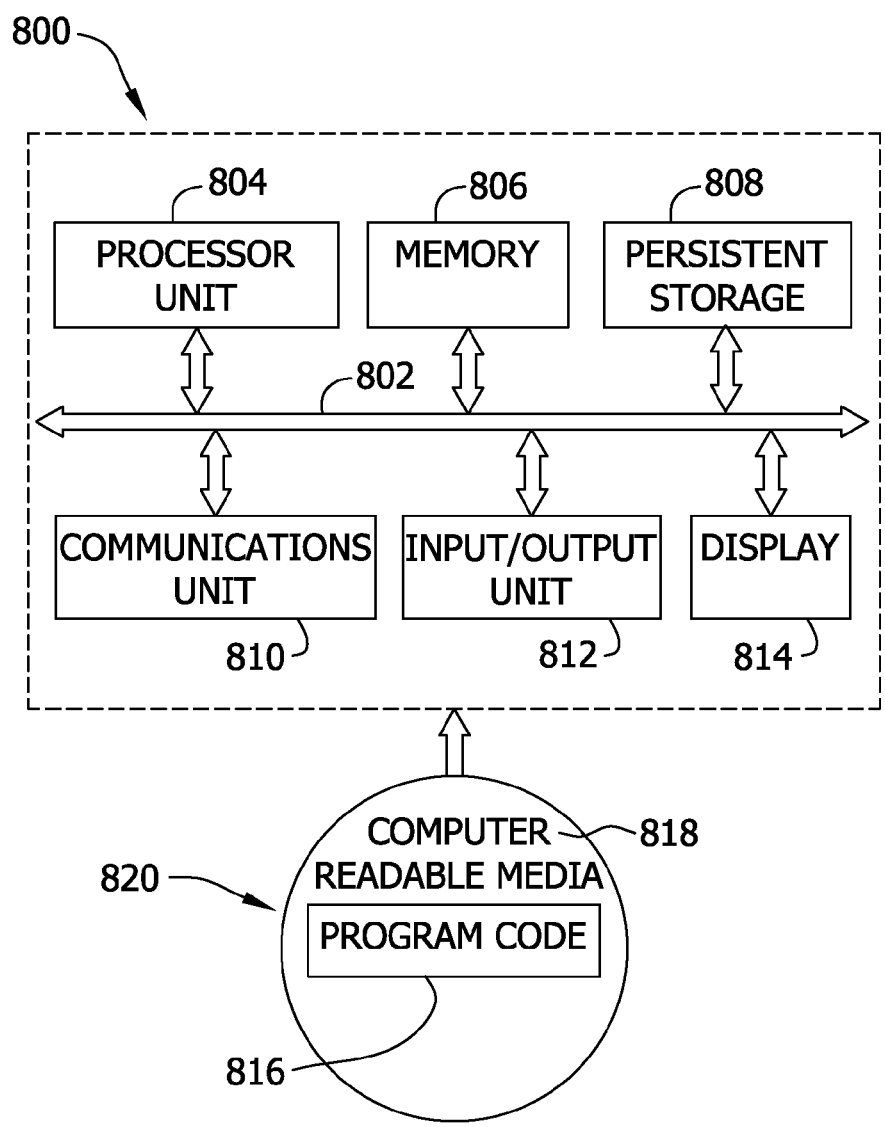
FIG. 15 is a diagram of a data processing system.

Turning now to FIG. 15, a diagram of a data processing system is depicted in accordance with an illustrative embodiment. In this illustrative example, data processing system 800 includes communications fabric 802, which provides communications between processor unit 804, memory 806, persistent storage 808, communications unit 810, input/output (I/O) unit 812, and display 814.

Processor unit 804 serves to execute instructions for software that may be loaded into memory 806. Processor unit 804 may be a set of one or more processors or may be a multi-processor core, depending on the particular implementation. Further, processor unit 804 may be implemented using one or more heterogeneous processor systems in which a main processor is present with secondary processors on a single chip. As another illustrative example, processor unit 804 may be a symmetric multi-processor system containing multiple processors of the same type.

Memory 806 and persistent storage 808 are examples of storage devices. A storage device is any piece of hardware that is capable of storing information either on a temporary basis and/or a permanent basis. Memory 806, in these examples, may be, for example, without limitation, a random access memory or any other suitable volatile or non-volatile storage device. Persistent storage 808 may take various forms depending on the particular implementation. For example, without limitation, persistent storage 808 may contain one or more components or devices. For example, persistent storage 808 may be a hard drive, a flash memory, a rewritable optical disk, a rewritable magnetic tape, or some combination of the above. The media used by persistent storage 808 also may be removable. For example, without limitation, a removable hard drive may be used for persistent storage 808.

Communications unit 810, in these examples, provides for communications with other data processing systems or devices. In these examples, communications unit 810 is a network interface card. Communications unit 810 may provide communications through the use of either or both physical and wireless communication links.

Input/output unit 812 allows for input and output of data with other devices that may be connected to data processing system 800. For example, without limitation, input/output unit 812 may provide a connection for user input through a keyboard and mouse. Further, input/output unit 812 may send output to a printer. Display 814 provides a mechanism to display information to a user.

Instructions for the operating system and applications or programs are located on persistent storage 808. These instructions may be loaded into memory 806 for execution by processor unit 804. The processes of the different embodiments may be performed by processor unit 804 using computer implemented instructions, which may be located in a memory, such as memory 806. These instructions are referred to as program code, computer usable program code, or computer readable program code that may be read and executed by a processor in processor unit 804. The program code in the different embodiments may be embodied on different physical or tangible computer readable media, such as memory 806 or persistent storage 808.

Program code 816 is located in a functional form on computer readable media 818 that is selectively removable and may be loaded onto or transferred to data processing system 800 for execution by processor unit 804. Program code 816 and computer readable media 818 form computer program product 820 in these examples. In one example, computer readable media 818 may be in a tangible form, such as, for example, an optical or magnetic disc that is inserted or placed into a drive or other device that is part of persistent storage 808 for transfer onto a storage device, such as a hard drive that is part of persistent storage 808. In a tangible form, computer readable media 818 also may take the form of a persistent storage, such as a hard drive, a thumb drive, or a flash memory that is connected to data processing system 800. The tangible form of computer readable media 818 is also referred to as computer recordable storage media. In some instances, computer readable media 818 may not be removable.

Alternatively, program code 816 may be transferred to data processing system 800 from computer readable media 818 through a communications link to communications unit 810 and/or through a connection to input/output unit 812. The communications link and/or the connection may be physical or wireless in the illustrative examples. The computer readable media also may take the form of non-tangible media, such as communications links or wireless transmissions containing the program code.

In some illustrative embodiments, program code 816 may be downloaded over a network to persistent storage 808 from another device or data processing system for use within data processing system 800. For instance, program code stored in a computer readable storage medium in a server data processing system may be downloaded over a network from the server to data processing system 800. The data processing system providing program code 816 may be a server computer, a client computer, or some other device capable of storing and transmitting program code 816.

The different components illustrated for data processing system 800 are not meant to provide architectural limitations to the manner in which different embodiments may be implemented. The different illustrative embodiments may be implemented in a data processing system including components in addition to or in place of those illustrated for data processing system 800. Other components shown in FIG. 8 can be varied from the illustrative examples shown.

As one example, a storage device in data processing system 800 is any hardware apparatus that may store data. Memory 806, persistent storage 808 and computer readable media 818 are examples of storage devices in a tangible form.

In another example, a bus system may be used to implement communications fabric 802 and may be comprised of one or more buses, such as a system bus or an input/output bus. Of course, the bus system may be implemented using any suitable type of architecture that provides for a transfer of data between different components or devices attached to the bus system. Additionally, a communications unit may include one or more devices used to transmit and receive data, such as a modem or a network adapter. Further, a memory may be, for example, without limitation, memory 806 or a cache such as that found in an interface and memory controller hub that may be present in communications fabric 802.

This written description uses examples to disclose various embodiments, which include the best mode, to enable any person skilled in the art to practice those embodiments, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method for compensating for environment induced variations in structural health monitoring application data, said method comprising:
   imparting a vibration signal onto a structure at a first location, the structure at a first temperature;
   receiving a comparison signal at a second location of the structure, the comparison signal resulting from the vibration signal;
   accessing data representing a reference signal, the reference signal previously received at the second location, based on an imparted vibration at the first location, the reference signal received when the structure was at a second temperature;
   dividing the comparison signal and the reference signal across a plurality of time windows;
   performing a cross correlation between the comparison signal and the reference signal in each time window by recording an amount of time shift required to maximally correlate the comparison signal and the reference signal within each time window;
   performing a weighted regression on time to estimate time delay, the weights based on a relative amount of signal energy from the reference signal in each time window, to determine a relationship between time and time shift as a quadratic or higher order equation, wherein a weight for higher signal energy in each time window is greater than a weight for lower signal energy in each time window; and
   using the determined relationship between time and time shift of the comparison signal to reduce the effects of environment on the comparison signal.

2. The method according to claim 1 wherein performing a weighted regression on time, the weights based on a relative amount of signal energy from the reference signal in each time window to determine a relationship between time and time shift, comprises adjusting any skew in a regression line based on an existence of one or more outliers in a received time shift of the comparison signal.

3. The method according to claim 1 further comprising:
   modeling time delay in received comparison signal data as a quadratic function of time;
   generating a regression curve of a resultant time delay data to learn coefficients of the quadratic function of time;
   recording an amount of time shift required to maximally correlate the comparison signal and the reference signal within each time window; and
   performing a weighted regression on time to estimate time delay.

4. The method according to claim 1 wherein performing a weighted regression on time comprises weighting the time shift calculated in each time window based on a normalized RMS value of the reference signal in each time window.

5. One or more non-transitory computer-readable storage media having computer-executable instructions embodied thereon, wherein when executed by at least one processor, the computer-executable instructions cause the at least one processor to:
   receive comparison signal data relating to a vibration experienced at a location of a structure, the comparison signal data resulting from a vibration signal imparted onto the structure at a different location, the comparison signal data generated when the structure is at a first temperature;
   access data representing a reference signal, the reference signal previously received at the structure location, and also based on an imparted vibration at the different location, the reference signal received when the structure was at a second temperature;
   divide the comparison signal and the reference signal across a plurality of time windows;
   perform a cross correlation between the comparison and reference signals in each of the time windows by recording an amount of time shift required to maximally correlate the two signals within each time window;
   perform a weighted regression, the weights based on the relative amount of signal energy from the reference signal in each time window, to determine a relationship between time and time delay as a quadratic or higher order equation, wherein a weight for higher signal energy in each time window is greater than a weight for lower signal energy in each time window; and
   use the relationship between time and time delay to reduce the effects of environment on the comparison signal.

6. One or more non-transitory computer-readable storage media having computer-executable instructions embodied thereon according to claim 5, wherein to weight the time shift between the comparison signal and the reference signal in each time window, the computer-executable instructions cause the at least one processor to adjust any skew in a regression line generated by the weighting of a comparison signal time shift based on an existence of one or more outliers in the received time shift of a comparison signal data.

7. One or more non-transitory computer-readable storage media having computer-executable instructions embodied thereon according to claim 5, wherein the computer-executable instructions cause the at least one processor to:
   model time delay in the received comparison signal data as a quadratic function of time; and
   generate a regression curve of the resultant time delay data to provide coefficients for a quadratic function of time.

8. One or more non-transitory computer-readable storage media having computer-executable instructions embodied thereon according to claim 5, wherein to perform a weighted regression based on the relative amount of signal energy from the reference signal within each time window, the computer-executable instructions cause the at least one processor to weight the time shift calculated for each time window based on a normalized RMS value of the reference signal in each window.

9. A method of compensating for temperature effects in a structural health monitoring system, said method comprising:
   compensating for nonlinear phase changes in a comparison signal, as compared to a reference signal, wherein a phase shift factor is replaced with a function;
   implementing, by a processor, a weighted regression of time shifts associated with the comparison signal across each of a plurality of time windows to determine parameters of the function, wherein a weight for higher signal energy in each time window is greater than a weight for lower signal energy in each time window;

implementing a time-shift outlier correction process onto the weighted regression; and processing the comparison signal using the function and the parameters determined for the function to provide output corresponding to a reduction in a stretch or a compression of the reference signal and the comparison signal.

10. The method according to claim 9 wherein compensating for nonlinear phase changes comprises modeling time delay in a received comparison signal data as a quadratic function of time.

11. The method according to claim 10 wherein implementing a weighted regression of time shifts associated with the comparison signal comprises:

dividing the comparison signal and the reference signal into time-based windows; and relatively weighting the time shifts of the comparison signal in each time-based window according to the signal energy associated with the reference signal in each time-based window.

12. The method according to claim 10 wherein implementing a time-shift outlier correction process comprises correcting the outlier by establishing a direction of correction by comparison with a data point associated with a time-based window having the highest energy.

* * * * *